United States Patent
Nissilä et al.

(10) Patent No.: US 7,477,934 B2
(45) Date of Patent: Jan. 13, 2009

(54) METHOD OF MONITORING HUMAN RELAXATION LEVEL, AND USER-OPERATED HEART RATE MONITOR

(75) Inventors: Seppo Nissilä, Oulu (FI); Hannu Kinnunen, Oulu (FI); Outi Hyyppä, Oulu (FI)

(73) Assignee: Polar Electro Oy, Kempele (FI)

(*) Notice: Subject to any disclaimer, the term of this patent is extended or adjusted under 35 U.S.C. 154(b) by 939 days.

(21) Appl. No.: 10/879,702

(22) Filed: Jun. 29, 2004

(65) Prior Publication Data

US 2006/0009701 A1    Jan. 12, 2006

(51) Int. Cl.
*A61B 5/04* (2006.01)
(52) U.S. Cl. .................................................. 600/509
(58) Field of Classification Search .................. 600/509, 600/526, 508, 520
See application file for complete search history.

(56) References Cited

U.S. PATENT DOCUMENTS

| | | | |
|---|---|---|---|
| 6,190,324 B1 * | 2/2001 | Kieval et al. ................. | 600/483 |
| 6,212,427 B1 | 4/2001 | Hoover | |
| 2002/0111555 A1 | 8/2002 | Stabler et al. | |
| 2004/0019289 A1 | 1/2004 | Ross | |

FOREIGN PATENT DOCUMENTS

EP    1 431 879 A2    6/2004

OTHER PUBLICATIONS

Task Force of The European Society of Cardiology and The North American Society of Pacing and Electrophysiology (Membership of the Task Force listed in the Appendix), "Heart rate variability," *European Heart Journal* 17:354-381, (1996).
European Search Report issued in European Patent Application No. EP 01504642.

* cited by examiner

*Primary Examiner*—Carl H Layno
*Assistant Examiner*—Brian T Gedeon
(74) *Attorney, Agent, or Firm*—Hoffmann & Baron, LLP

(57) ABSTRACT

A method of monitoring a human relaxation level and a user-operated heart rate monitor are provided. The user-operated heart rate monitor comprises a timing instant determining means for determining a plurality of heart beat timing instants from a user's electrocardiogram; a relaxation calculating means for calculating an instantaneous relaxation measure value by using the plurality of heart beat timing instants; a relaxation reference calculating means for generating a relaxation measure reference value by using a plurality of instantaneous relaxation measure values, each calculated over a different observation period; and a displaying means configured to display a reference pointer indicating graphically the relaxation measure reference value and further configured to display a relaxation pointer indicating graphically the instantaneous relaxation measure value relative to the reference pointer.

24 Claims, 7 Drawing Sheets

METHOD OF MONITORING HUMAN RELAXATION LEVEL, AND USER-OPERATED HEART RATE MONITOR

FIELD OF THE INVENTION

The invention relates to a method of monitoring a human relaxation level and to a user-operated heart rate monitor.

BRIEF DESCRIPTION OF THE RELATED ART

A person's relaxation level may be used as a measure of a person's exertion during and/or after a physical exercise. In heart rate monitor applications, the relaxation level may be obtained from the person's electrocardiogram, and the person may adjust an exertion level by monitoring his/her relaxation level from the heart rate monitor.

Even though the relaxation level may be used to characterize exertion in general, great variation may occur in relaxation characteristics, for example in the typical relaxation level, at different persons. As a result, a proper scaling of the relaxation level becomes a problem.

Therefore, it is useful to consider different solutions for monitoring human relaxation in heart rate monitor applications.

SUMMARY OF THE INVENTION

An object of the invention is to provide a method and a user-operated heart rate monitor such that the personal relaxation characteristics of a person are taken into account.

According to a first aspect of the invention, there is provided a user-operated heart rate monitor comprising: a timing instant determining means for determining a plurality of heart beat timing instants from a user's electrocardiogram; a relaxation calculating means for calculating an instantaneous relaxation measure value by using the plurality of heart beat timing instants; a relaxation reference generating means for generating a relaxation measure reference value by using a plurality of instantaneous relaxation measure values, each calculated over a different observation period; a displaying means configured to display a reference pointer indicating graphically the relaxation measure reference value; and wherein the displaying means is further configured to display a relaxation pointer indicating graphically the instantaneous relaxation measure value relative to the reference pointer.

According to a second aspect of the invention, there is provided a user-operated heart rate monitor comprising: a timing instant determining means for determining a plurality of heart beat timing instants from a user's electrocardiogram; a relaxation calculating means for calculating heart beat rate variation by using heart beat timing instants over an observation period, an instantaneous relaxation measure value being proportional to the heart beat rate variation; and a relaxation reference generating means for calculating a relaxation measure reference value by using a plurality of instantaneous relaxation measure values, each calculated over a different observation period; a displaying means configured to display a reference pointer indicating graphically the relaxation measure reference value; and wherein the displaying means is further configured to display a relaxation pointer indicating graphically the instantaneous relaxation measure value relative to the reference pointer.

According to a third aspect of the invention, there is provided a method of monitoring a human relaxation level comprising: determining a plurality of heart beat timing instants from a user's electrocardiogram; calculating an instantaneous relaxation measure value by using the plurality of heart beat timing instants; generating a relaxation measure reference value by using a plurality of instantaneous relaxation measure values, each calculated over a different observation period; displaying a reference pointer indicating graphically the relaxation measure reference value; and displaying a relaxation pointer indicating graphically the instantaneous relaxation measure value relative to the reference pointer.

According to yet another aspect of the invention, there is provided a method of monitoring a human relaxation level, comprising: determining a plurality of heart beat timing instants from a user's electrocardiogram; calculating heart beat rate variation by using heart beat timing instants over an observation period, an instantaneous relaxation measure value being proportional to the heart beat rate variation; generating a relaxation measure reference value by using a plurality of instantaneous relaxation measure values, each calculated over a different observation period; displaying a reference pointer indicating graphically the relaxation measure reference value; and displaying a relaxation pointer indicating graphically the instantaneous relaxation measure value relative to the reference pointer.

The invention provides several advantages. In an embodiment, the invention provides a personal relaxation reference value for the person's relaxation level, the relaxation reference being based on a plurality of instantaneous relaxation levels. The instantaneous relaxation level is displayed graphically along with the relaxation reference so that the user may relate the instantaneous relaxation level to his or her personal standard. Furthermore, a personalized relaxation monitoring enables the user so to adjust the exertion level according to his or her personal needs.

BRIEF DESCRIPTION OF THE DRAWINGS

In the following, the invention will be described in greater detail with reference to the embodiments and the accompanying drawings, in which.

DETAILED DESCRIPTION OF THE PREFERRED EMBODIMENTS

Figure 1:
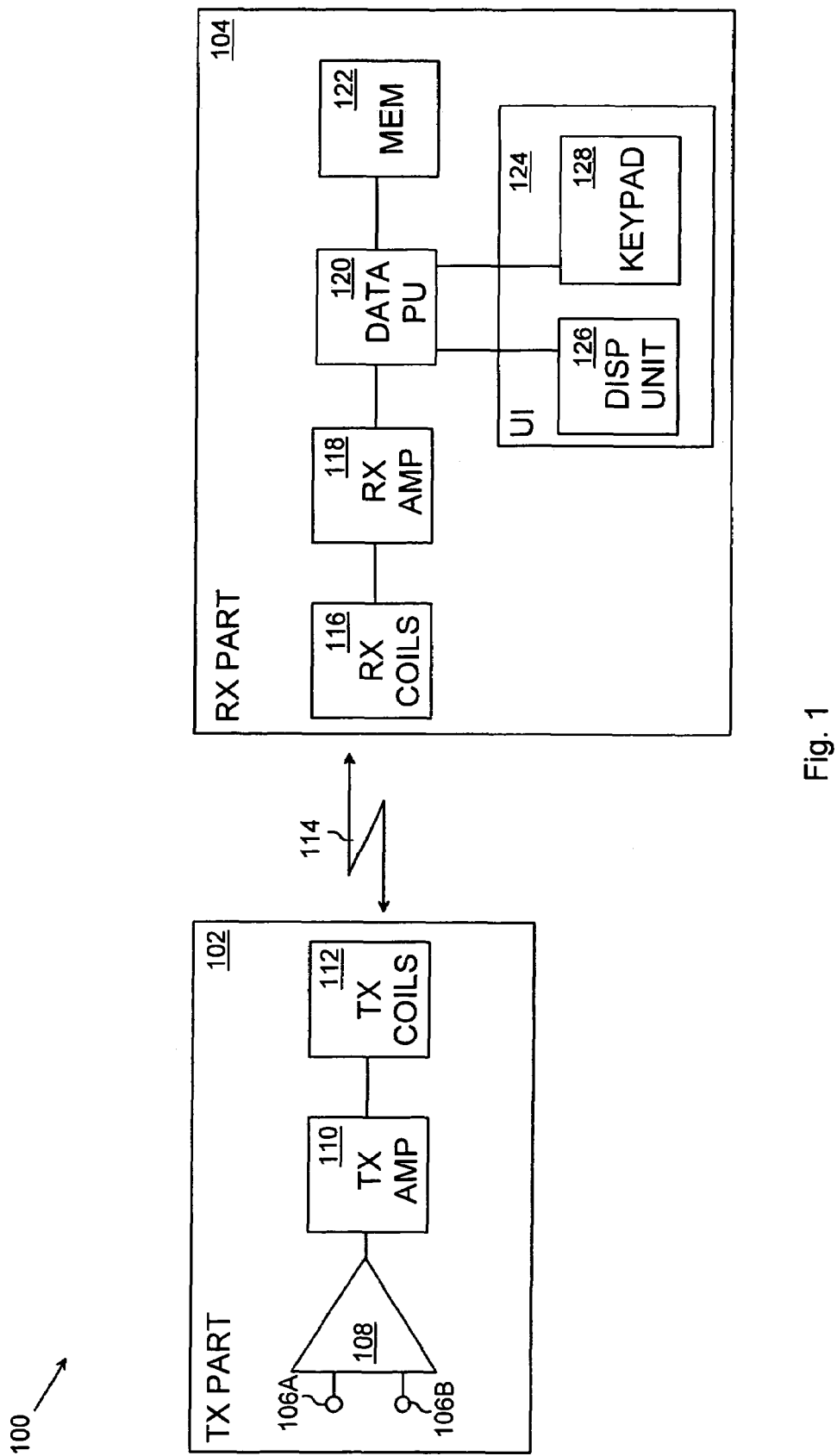
FIG. 1 is a block diagram illustrating an example of an ECG monitoring system.

FIG. 1 shows an example of a structure of a telemetry-based ECG (Electrocardiogram) monitoring system 100. The ECG monitoring system 100 comprises electrodes 106A, 106B, an ECG preamplifier 108 equipped with differential input poles, a transmit amplifier 110, a transmit coil unit 112, a receive coil unit 116, a receive amplifier 118, a data processing unit 120, a memory unit 122, and a user interface 124.

The electrodes 106A, 106B probe the electric potent generated by the electric activity of the heart, thus-producing an ECG signal characterizing the extra-cellular electric behavior of the cardiac muscle tissue and providing information on the human relaxation level.

The electrodes 106A, 106B may be connected to the differential input poles of the ECG preamplifier 108. An ECG signal supplied by the ECG preamplifier 108 is amplified in the transmit amplifier 110 unit. The transmit amplifier unit 110 may include an AGC (Automatic Gain Control) amplifier and a power amplifier.

The transmit coil unit 112 generates an electromagnetic field 114 transferring ECG information generated from the ECG detected by the electrodes 106A, 106B. The ECG information may include an ECG as such, a portion of the ECG, and/or heart beat timing information. The timing information may include a timing pulse indicating physically a timing of a predefined portion of an ECG.

In this example, the magnetic component of the electromagnetic field 114 acts as a wireless communication carrier.

The receiver coil unit 116 detects the magnetic field generated by the transmit coil unit 114, generates an induced electric signal, and inputs the electric signal into the receive amplifier unit 118.

In some embodiments of the invention, conventional radio telemetry may be used instead of magnetic telemetry.

The receive amplifier unit 118 carries out signal processing, such as filtering and amplifying, and supplies the electric signal to the data processing unit 120. The receive amplifier unit 118 may include a series of successive regulating stages. The electric signal outputted by the receive amplifier unit 118 carries the ECG information.

The data processing unit 120 processes the electric signal. Data processing may include analog data processing, such as analog filtering, and digital data processing, such as digital filtering, signal shaping, signal detection, and analyzing the electric signal. The data processing unit 120 may further comprise an analog-to-digital converter.

Portions of the electric signal and processing results may be stored temporarily or permanently in a memory unit 122 connected to the data processing unit 120. The memory unit 122 may include computer programs executed in the data processing unit 120.

The data processing unit 120 may include analog circuits, ASIC (Application Specific Integrated Circuit), a digital processor, registers, memory, and software.

The user interface 124 includes a display unit 126 comprising a display, such as an LCD (Liquid Crystal Display), and a display controller. In some applications, the display controller may be integrated into the data processing unit 120. The display unit 124 shows graphically, for example, information generated from the user's ECG.

A keypad 128 allows the user to enter commands into the heart rate monitoring system 100.

With further reference to FIG. 1, the telemetry-based ECG monitoring system 100 may be divided into a transmitter part 102 and a receiver part 104. The transmitter part 102 typically includes device parts 106A to 112 and is responsible of an ECG measurement and a transmission of the ECG information to the receiver part 104. In some embodiments, the transmitter part 102 may include a pulse detector for detecting a predefined part of an ECG and generating a signal burst and/or a bit stream representing the timing of a predefined portion of an ECG pulse.

The receiver part 104 typically includes device parts 116 to 128 shown in FIG. 1, which are responsible for processing the ECG information and providing a user interface for the user.

Figure 2:
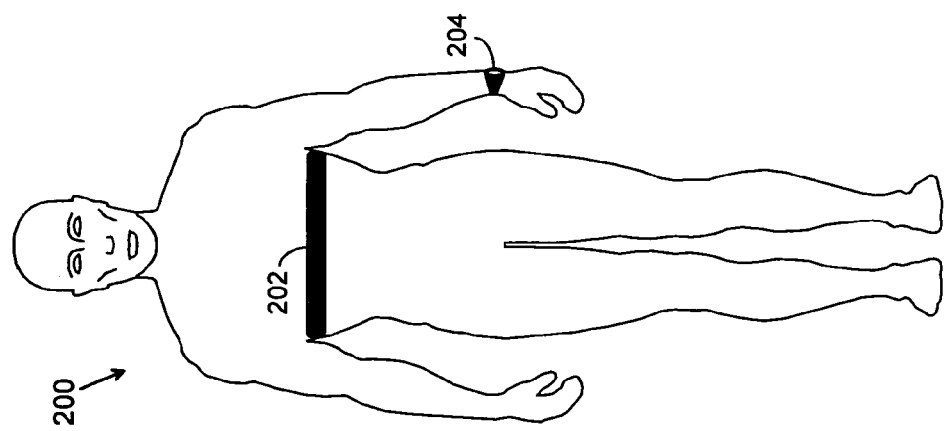
FIG. 2 shows an example of an ECG monitoring system installed to monitor a person.

With reference to an embodiment shown in FIG. 2, the transmitter part 102 is placed in a transmitter belt 202 placed around the chest of a person 200. The ECG information is telemetrically and wirelessly transmitted from the transmitter belt 202 to the receiver unit 204, which may be implemented as a receiver wristband worn on the wrist of the person 200. When applied to a cycling exercise for example, the receiver unit 204 may be attached to the hand-bar or other structure of the bicycle. The location of the receiver unit 204 is, however, not restricted to the wrist or the hand-bar but may be chosen freely, provided that the wireless communication between the transmitter part 102 and the receiver part 104 is possible and the user is capable of operating the receiver part 104.

In an embodiment of the invention, the transmitter part 102 and the receiver part 104 are integrated inside a single housing, constituting a unit with a wristband to be worn for instance exclusively on the wrist or for instance exclusively on the hand-bar of a bicycle. In such a system, the coil units 112, 116 and some of the amplifier units 110, 118 may not be required.

The user-operated heart rate monitor may be used during a physical exercise or in another situation where a moving user typically requires instantaneous relaxation level information.

A user-operated heart rate monitor comprises at least a receiver part 104. In an embodiment of the invention, the user-operated heart rate monitor comprises the transmitter part 102 and the receiver part 104.

A characteristic of a user-operated heart rate monitor is that the person whose relaxation level is being monitored operates the heart rate monitor via the user interface 124.

Figure 3:
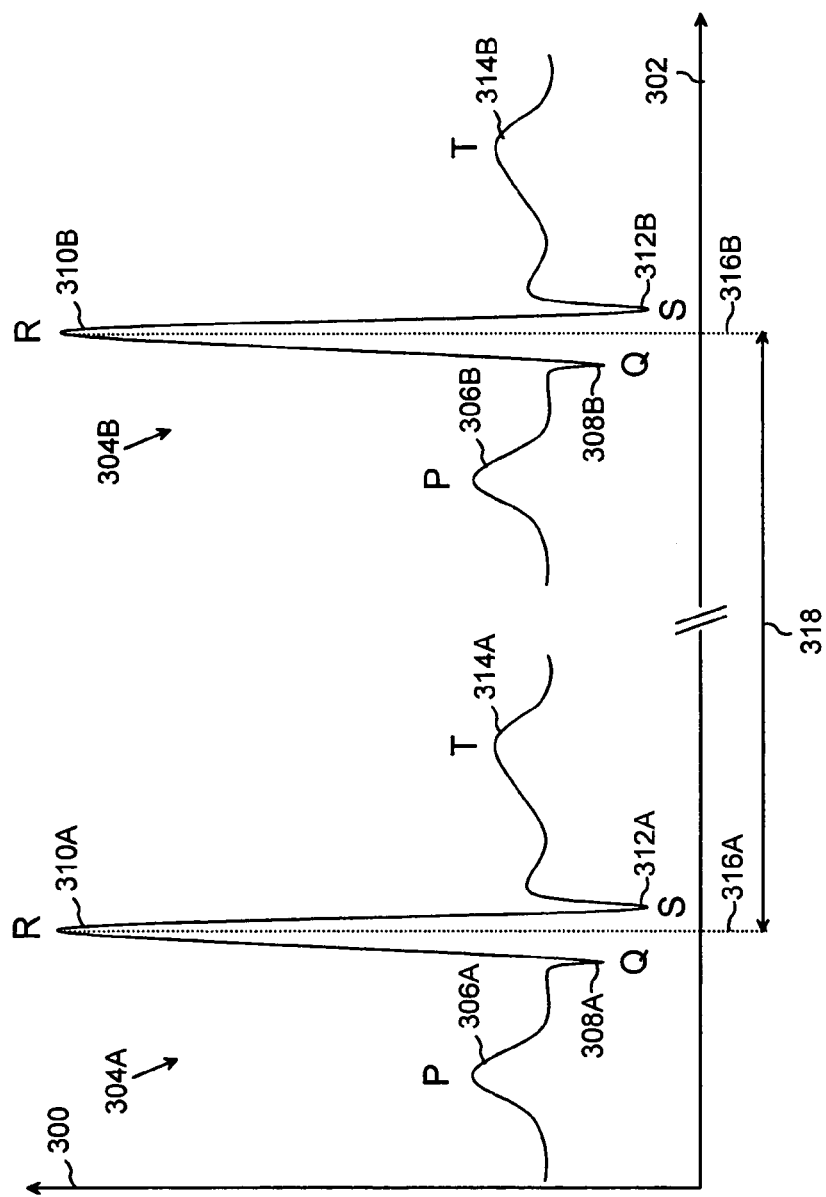
FIG. 3 shows an example of a portion of an ECG.

FIG. 3 shows successive pulses 304A, 304B and pulse characteristics of a typical ECG presented in a time-voltage coordinate system 300, 302.

Each pulse 304A, 304B corresponds to a heart beat associated with a heart beat timing instant 316A, 316B. A time interval 318 between successive pulses 304A, 304B is referred to as a heart beat interval 318.

A pulse 304A, 304B is typically characterized with a P-wave 306A, 306B a Q-wave 308A, 308B, an R-wave 310A, 310B, an S-wave 312A, 312B, and/or a T-wave 314A, 314B, which waves represent various stages of the work cycle of the cardiac muscle.

The R-wave 310A, 310B represents the maximum point of the ECG, and the combination of Q-, R-, and S-waves, also referred to as a QRS complex, provides an easily distinguishable part of the pulse 304A, 304B.

The P-wave 306A, 306B is caused by a contraction of the atria. The QRS complex is generated when the ventricles contract. The re-polarization of the ventricle muscles gives rise to the T-wave 314A, 314B, which is lower and more even than the R-wave 310A, 310B.

In a healthy human, the ECG signal is typically between 1 mV and 2 mV in amplitude when measured on the skin. For instance, the amplitude value and duration at an R-wave maximum are typically 1.6 mV and 90 ms, respectively, whereas the amplitude value and duration at a P-wave maximum are 0.25 mV and 110 ms, respectively. As the heartbeat rate accelerates as a result of physical exercise, for example, the durations and amplitudes of the characteristic components of the ECG remain almost unchanged. It is thus known that accurate measurement of heart beat and related phenomena is possible by analyzing the ECG.

In a disturbance-free situation, the QRS complex may be detected by means of a peak value detector. A filter arrangement, such as a band-pass filter and/or an adapted filter may be used to reduce disturbances that may take place in practical situations.

Figure 4:
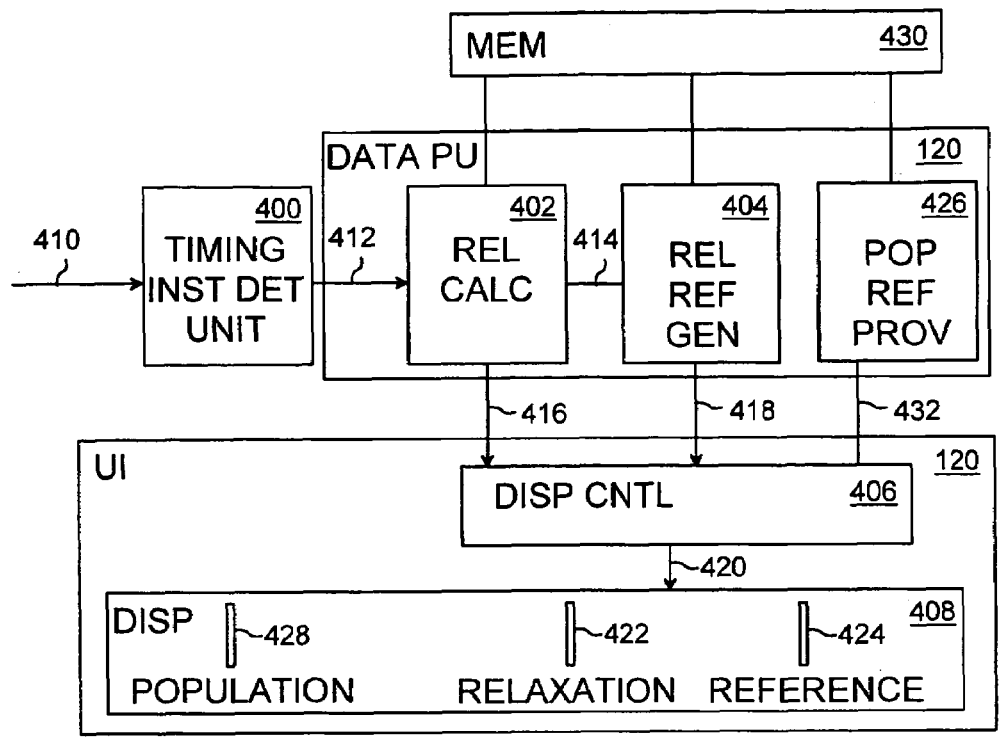
FIG. 4 shows an example of a data processing unit, a memory unit, and a display of a heart rate monitor.

With reference to an example shown in FIG. 4, the heart rate monitor includes a timing instant determination unit 400 for determining the heart beat timing instants 316A, 316B.

The timing instant determination unit 400 receives an ECG signal 410 and identifies, for example, the QRS complexes of the pulses 304A, 304B.

The timing instant determination unit 400 may then search for an R-wave maximum, and the R-wave maximum may be selected to represent a timing point of the ECG. The timing instant determination unit 400 may, however, search for other parts of the pulses 304A, 304B, the other parts having timing points.

A timing instant 316A, 316B may be determined relative to a general time reference of the heart rate monitor and/or relative to timing instants of other pulses 304A, 304B.

In an embodiment of the invention, the timing instant 316A, 316B is determined relative to a previous pulse 304A, 304B. In such a case, a heart beat time instant 316B equals the heart beat interval 318.

Some parts of the timing instant determination unit 400 may be implemented with a digital processor and software. In an embodiment of the invention, some parts of the timing instant determination unit 400 are implemented with ASIC.

The timing instant determination unit 400 may be physically distributed in the transmitter part 102 and the receiver part 104. In an embodiment of the invention, the transmitter part 102 includes a pulse detector detecting the QRS complexes, for example. Time stamping .i.e. assigning a timing instant to the QRS complexes, may be done in the receiver unit 104.

Heart beat timing instant information 412 is fed into a relaxation calculator 402 that calculates an instantaneous relaxation measure value by using the heart beat timing instants 316A, 316B.

The instantaneous relaxation measure value is typically proportional to heart rate variation. Heart rate variation may be obtained by recording a plurality of heart rate values over an observation period, calculating a statistical characteristic, such as a heart rate average, representing the heart rate value during the observation period, and investigating a statistical deviation of the group of individual heart rate values relative to the statistical characteristics. The observation period may vary from 1 minute to 5 minutes being, however, not restricted to the given figures.

A relaxation measurement is typically done during a stage of a sports session where the user attempts to recover after a physical exercise and/or is preparing for a physical exertion.

In an embodiment of the invention, the instantaneous relaxation measure value $S_k$ for the $k^{th}$ observation period may be expressed as $$S_k = S_k(R_1, \ldots, R_N, R_A), \quad (1)$$

where $R_1, \ldots, R_N$ represent individual heart rate values observed during the observation period, and $R_A$ represents a statistical characteristic, such as the average of the heart rate, representing the heart rate over the $k^{th}$ observation period. Factor N is the number of observations of the heart rates.

In an embodiment of the invention, the instantaneous relaxation measure value is proportional to a statistical deviation, such as a standard deviation, of the heart rate value. In mathematical terms, the relaxation measure value may be in this case expressed as $$S_k \sim \sqrt{\frac{\sum (R_i - R_A)^2}{SC}}, \quad (2)$$

where SC is a scaling factor proportional to N or N−1, for example.

In an aspect of the invention, the instantaneous relaxation measure value is proportional to a statistical deviation of heart beat intervals 318 relative to a heart beat interval average. In this case, a plurality of heart beat intervals 318 are determined by the timing instant determination unit 400 and/or the relaxation calculator 402. A statistical average of the heart beat intervals is taken during an observation period in the relaxation calculator 402 and the statistical deviation, such as standard deviation, related to the statistical average is calculated from the individual heart beat intervals 318. With reference to Equation (2), terms $R_i$ represent the individual heart beat intervals 318 and term $R_A$ represents the heart beat interval average.

The relaxation calculator 402 may store the individual heart rate values and/or heart beat intervals in the memory unit 430 during the observation period and use stored figures when calculating the relaxation measure value according to Equation (2), for example. The calculated relaxation measure value $S_k$ may be stored in the memory unit 430 for further processing.

It should be noted that the relaxation level may be expressed in the time domain or in the frequency domain. In both cases, a large deviation in the heart rate and heart beat interval indicates a high relaxation level whereas a small deviation indicates a low relaxation level.

The relaxation calculator 402 may be implemented with a digital processor, software, and memory.

The data processing unit 120 further comprises a relaxation reference generator 404 connected to the relaxation calculator 402. The relaxation reference generator 404 uses instantaneous relaxation measure values as input and calculates a relaxation reference value by using the instantaneous relaxation measure values. The instantaneous relaxation measure values may be retrieved from the memory unit 430 or received from the relaxation calculator 402 in an input signal 414.

A relaxation measure reference value provides a user-specific benchmark for the instantaneous relaxation measure value. By using the relaxation measure reference value, the user is capable of adjusting the exertion level according to his or her personal needs.

In an embodiment of the invention, the relaxation reference generator 404 calculates the relaxation measure reference value as an average of the plurality of instantaneous relaxation measure values. With mathematical terms, this may be expressed as $$S_{REF} = \frac{\sum S_k}{M}, \quad (3)$$

where $S_{REF}$ is the relaxation measure reference value and M is the number of observation periods used in a summation, each observation period having an instantaneous relaxation measure value $S_k$.

The observation periods and the instantaneous relaxation measure values $S_k$ used in the calculation of the relaxation measure reference value may be selected on the basis of various criteria.

In an embodiment of the invention, the relaxation measure reference value is calculated separately for each sports session, such as a run. In such a case, the relaxation measure reference value calculation may be triggered when the user switches on the relaxation calculation mode in the heart rate monitor.

In another embodiment of the invention, the heart rate monitor stores instantaneous relaxation measure reference values calculated for several sports sessions. The relaxation reference generator 404 may calculate an average from stored relaxation measure reference values and/or select an appropriate value, such as that indicating the largest relaxation level, as a current relaxation measure reference value.

In an embodiment of the invention, the relaxation reference generator 404 selects the relaxation measure reference value from the plurality of instantaneous relaxation measure values on the basis of the magnitudes of the instantaneous relaxation measure values. For example, the relaxation reference generator 404 may compare the instantaneous relaxation measure values stored in the memory unit 430 and select the maximum instantaneous relaxation measure value as a relaxation measure reference value. The maximum relaxation measure value corresponds to the largest value of the statistical deviation in the heart rate or in the heart beat interval, i.e. the highest relaxation level. In some embodiments, the median of the instantaneous relaxation measure values is selected as the relaxation measure reference value.

The relaxation reference generator 404 may be implemented with a digital processor, memory, and software.

The relaxation reference generator 404 inputs the relaxation measure reference value 418 into a display controller 406.

The relaxation calculator 402 inputs the instantaneous relaxation measure value 416 into the display controller 406.

The display controller 406 generates a control signal 420 that includes instructions to display graphically a reference pointer 424 and a relaxation pointer 422 relative to the reference pointer 424 on the basis of the relaxation measure reference value 418 and the instantaneous relaxation measure value 416.

The reference pointer 424 indicates graphically the relaxation measure reference value.

The relaxation pointer 422 indicates graphically the instantaneous relaxation measure value relative to the reference pointer 424.

When the relaxation pointer 422 is indicated relative to the reference pointer 424, the user is capable of adjusting the exertion level such that the relaxation level relates to the relaxation reference level in a desired manner. The user may, for example, use the relaxation level indicated by the reference pointer 424 as a target value for the instantaneous relaxation level.

The display controller 406 may be implemented with a digital processor and software. Some parts of the display controller may be implemented with ASIC.

In an embodiment of the invention, the heart rate monitor comprises a population reference provider 426 for providing at least one population reference value characterizing a relaxation measure value of at least one human population. The population reference provider 426 may include a database of typical relaxation measure values of various populations categorized according to variables such as, age, gender, sports, or other characteristic the user may be associated with. The user may select the population reference value from a suitable category.

The population reference provider 426 inputs a control signal 432 into the display controller 406, the control signal 432 including instructions for displaying the population pointer 428 on the display 408.

In an embodiment of the invention, the population reference provider 426 uses data representing the population reference value as a function of a variable, such as age, to generate a suitable population reference value. This may be required if the database does not contain the population reference value for the user's exact age. In such a case, interpolation procedures may be applied to generate the suitable population reference value.

The population reference provider 426 may be implemented with a digital processor, memory, and software.

The user may select an appropriate category and command the heart rate monitor to display a population pointer 428 indicating the population reference value graphically on the display 408.

Figure 5:
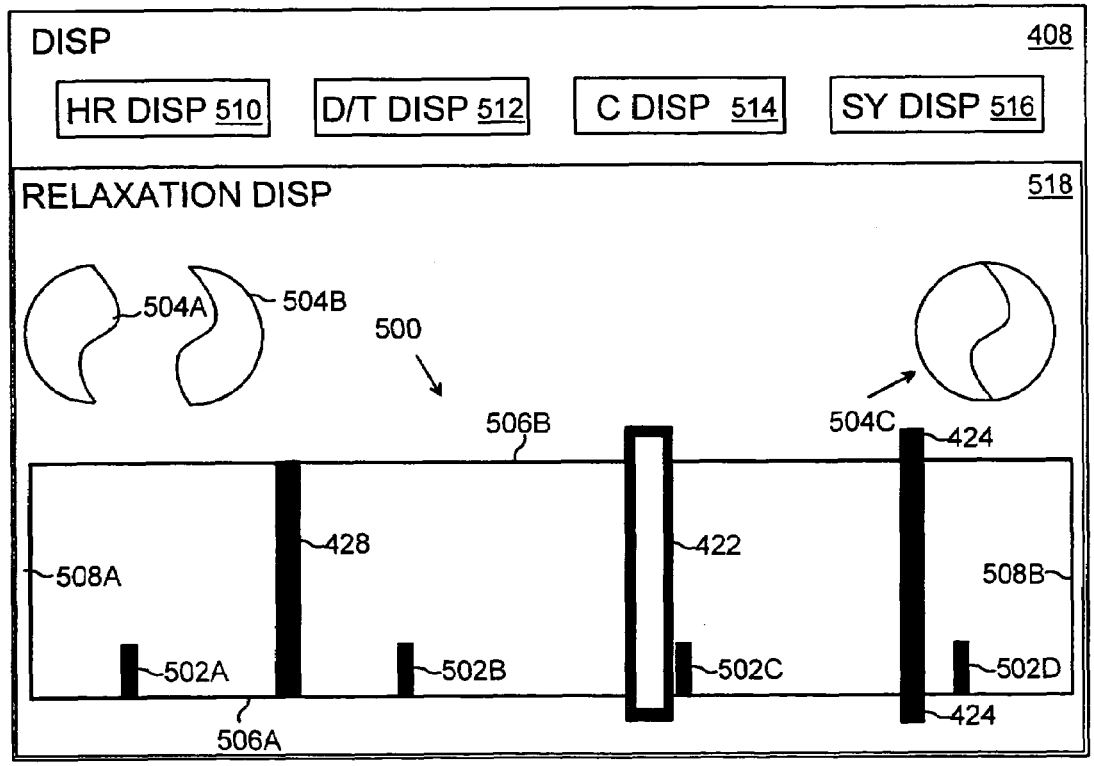
FIG. 5 shows an example of an embodiment of a display of a heart rate monitor.

With reference to FIG. 5, the display 408 may include a heart rate segment 510, a date/time segment 512, a control segment 514, and a symbol segment 516.

The heart rate segment 510 may display the instantaneous heart rate and/or average heart rate graphically and/or with numeric symbols.

The date/time segment 512 may display date and/or time with numeric symbols.

The control segment 514 may display menu items and instantaneous status information on the functions the heart rate monitor performs.

The symbol segment 516 may display graphical symbols indicating, for example, an ongoing heart rate measurement.

The heart rate monitor may further include a relaxation display segment 518 displaying the reference pointer 424, the relaxation pointer 422 and the population pointer 428.

In an embodiment of the invention, the display 408 includes a relaxation scale 506A with tick marks 502A to 502D. The relaxation pointer 422 and the reference pointer 424 are displayed relative to the relaxation scale 506A in order to provide a common scale for the reference pointer 424 and the relaxation pointer 422 and to ease up monitoring user's instantaneous relaxation level. The relaxation scale 506A may be horizontally oriented and the relaxation indicator 428 moves horizontally according to the instantaneous relaxation measure value. The reference pointer 424 and the population pointer 428 are horizontally located according to the relaxation measure reference value, and the population reference value, respectively.

In another embodiment of the invention, the relaxation scale 506A is vertically oriented and the relaxation pointer 424, the reference pointer 422, and the population pointer 428 move vertically according to the relaxation measure value, the relaxation measure reference value, and the population reference value, respectively.

The relaxation scale 506A includes a low end and a high end. The low end corresponds to a low relaxation level, i.e. a high stress level. The high end corresponds to a high relaxation level, i.e. a low stress level. The low end and the high end provide scaling information for scaling the relaxation scale 506A.

In an embodiment of the invention, the relaxation scale 506A is displayed in millisecond units. A separation of successive tick marks 502A to 502D may be 10 milliseconds or a multiple of 10 milliseconds, without limiting the separation to given figures.

In an embodiment of the invention the relaxation scale 506A is displayed in a frequency unit, such as one beat per minute (bpm) unit. Successive tick marks 502A to 502D may be separated from one to another by intervals of 20 bpm or 50 bpm, the separation not being, however, limited to these figures.

The low end of the relaxation scale 506A may be fixed at 0 to 10 milliseconds, thus corresponding to low relaxation level, without limiting a fixing to given figures.

In frequency units, the low end of the relaxation scale 506A may be fixed at 40 bpm to 50 bbp, the fixing not being, however, limited to these figures.

The low end of the relaxation scale 506A may also be fixed at the minimum relaxation measure value measured during any observation period.

In an embodiment of the invention, the low end of the relaxation scale 506A is fixed to a value proportional to the relaxation measure reference value. This value may be 10%, for example, of the relaxation measure reference value.

The high end of the relaxation scale 506A may be fixed at 80 to 100 milliseconds, thus corresponding to a high relaxation level. In frequency units, the high end of the relaxation scale 506A may be fixed at 200 bpm to 240 pbm, the fixing not being, however, limited to these figures.

In an embodiment of the invention, the high end of the relaxation scale 506A is fixed at the highest measured user's relaxation measure value.

In another embodiment of the invention, the high end of the relaxation scale 506A is fixed at a value proportional to the relaxation measure reference value. Such a value may be, 150% for example, of the relaxation measure reference value.

The information for fixing the low end and the high end of the relaxation scale 506A may be obtained from the memory unit 430 that may include a register for storing updated relaxation measure values and relaxation measure reference values. The updated relaxation measure values and relaxation measure reference values may be provided for the display controller 406 that delivers the scaling information to the display 408 by using the control signal 420.

FIG. 5 shows graphical symbols 504A to 504C indicating the direction of the relaxation scale 506A. The graphical symbols 504A to 504C may be Ying Yang symbols that are used to symbolize a relaxation level. In the example of FIG. 5, the left end of the relaxation scale 506A corresponds to a low relaxation level whereas the right end corresponds to a high relaxation level.

FIG. 5 further shows an elongated scale area 500 defined by long sides 508A, 508B and long sides 506A, 506B. The tick marks 502A to 502D indicate the relaxation scale in the elongated scale area 500.

The elongated scale area 500 provides an easily identifiable structure in the display 408 of the heart rate monitor. The elongated display area 500 may be formed by a uniform display element, such as an LCD element. Graphical elements, such as the pointers 422, 424, 428, the relaxation scale 504A, the tick marks 502A to 502D, and the graphical symbols 504A to 504C, are formed by a combination of pixels of the LCD element.

The relaxation pointer 422, the reference pointer 424, and the population pointer 428 are movable in the direction of the long sides 506A, 506B and typically overlap the elongated display area 500.

The relaxation pointer 422, the reference pointer 422, and the population pointer 428 may have bar-like structures where a bar is essentially perpendicular to the long sides 506A, 506B.

The relaxation pointer 422, the reference pointer 422, and the population pointer 428 may be graphically different to make them more easily recognizable and distinguishable from one another.

With reference to FIGS. 6, 7, 8, and 9 examples of the methodology according to the embodiments of the invention are illustrated with block diagram presentation.

Figure 6:
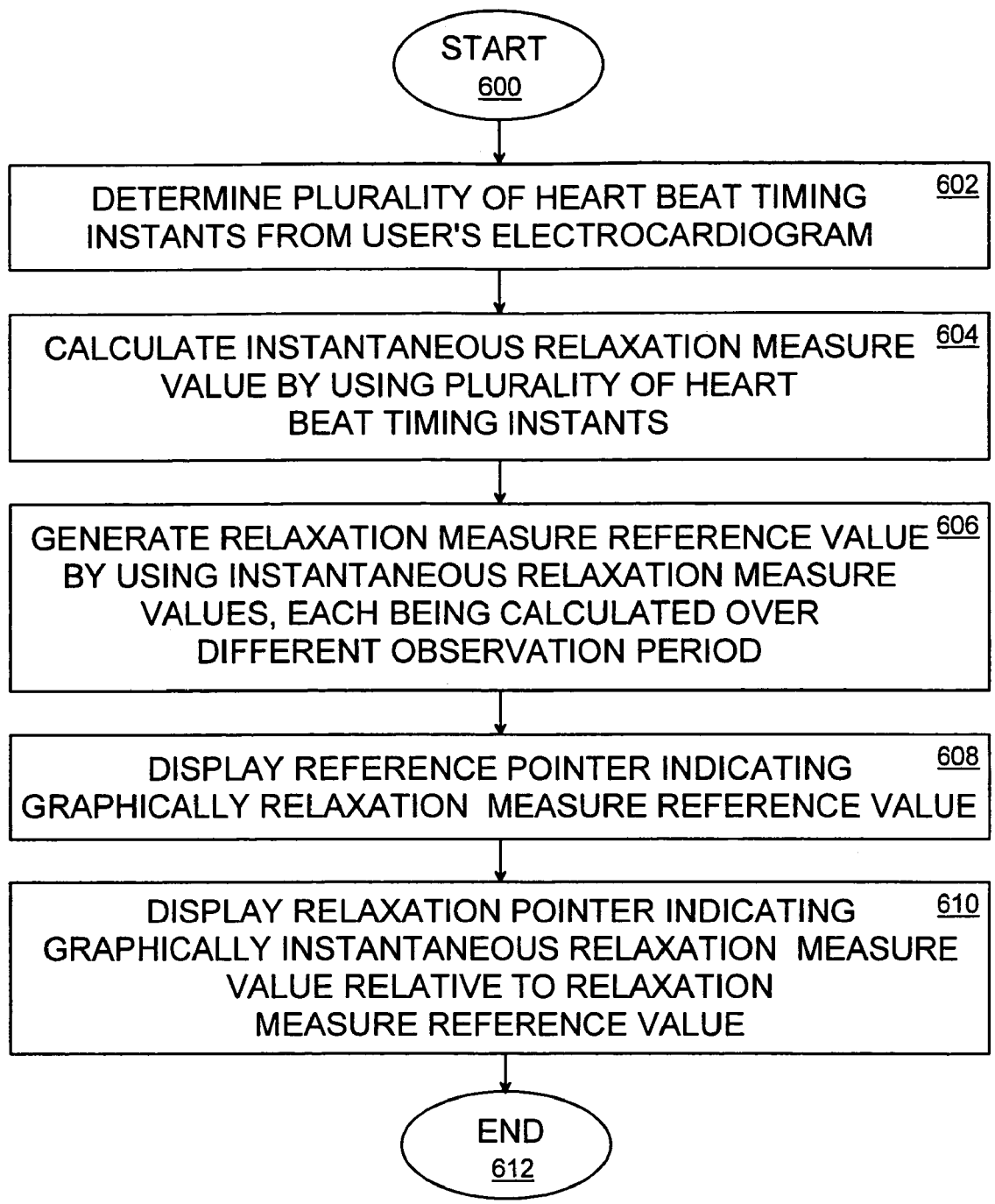
FIG. 6 shows a first example of a methodology according to embodiments of the invention.

In FIG. 6, the method starts in 600.

In 602, a plurality of heart beat timing instants 316A, 316B is determined from a user's electrocardiogram.

In 604, an instantaneous relaxation measure value is calculated by using the plurality of heart beat timing instants 316A, 316B.

In 606, a relaxation measure reference value is generated by using a plurality of instantaneous relaxation measure values, each calculated over a different observation period. In an embodiment of the invention, the relaxation measure reference value is generated by calculating the relaxation measure reference value as an average of the plurality of instantaneous relaxation measure values. In another embodiment of the invention, the relaxation measure reference value is generated by selecting the relaxation measure reference value from the plurality of instantaneous relaxation measure values on the basis of the magnitudes of the instantaneous relaxation measure values.

In 608 a reference pointer 424 is displayed, the reference pointer 424 indicating graphically the relaxation measure reference value.

In 610, a relaxation pointer 422 is displayed, the relaxation pointer 422 indicating graphically the instantaneous relaxation measure value relative to the reference pointer 424.

In 612, the method ends.

Figure 7:
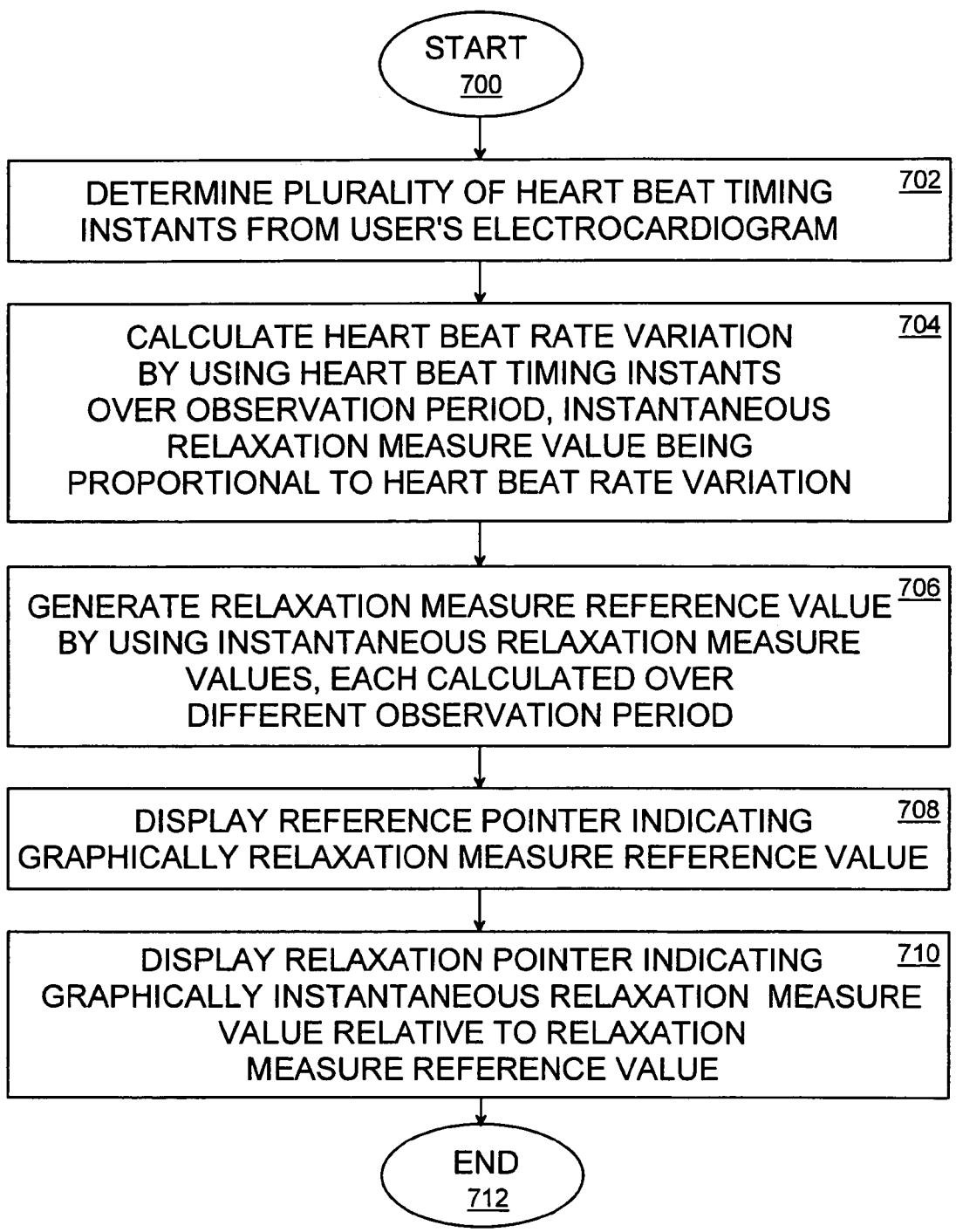
FIG. 7 shows a second example of a methodology according to embodiments of the invention.

In FIG. 7, the method starts in 700.

In 702, a plurality of heart beat timing instants 316A, 316B is determined from a user's electrocardiogram.

In 704, a statistical deviation of heart beat intervals 318 is calculated relative to a heart beat interval average by using heart beat timing instants 316A, 316B over an observation period, an instantaneous relaxation measure value being proportional to the statistical deviation.

In 706, a relaxation measure reference value is generated by using a plurality of instantaneous relaxation measure values, each calculated over a different observation period. In an embodiment of the invention, the relaxation measure reference value is generated by calculating the relaxation measure reference value as an average of the plurality of instantaneous relaxation measure values. In another embodiment of the invention, the relaxation measure reference value is generated by selecting the relaxation measure reference value from the plurality of instantaneous relaxation measure values on the basis of the magnitudes of the instantaneous relaxation measure values.

In 708 a reference pointer 424 is displayed, the reference pointer 424 indicating graphically the relaxation measure reference value.

In 710, a relaxation pointer 422 is displayed, the relaxation pointer 422 indicating graphically the instantaneous relaxation measure value relative to the reference pointer 424.

In 712, the method ends.

Figure 8:
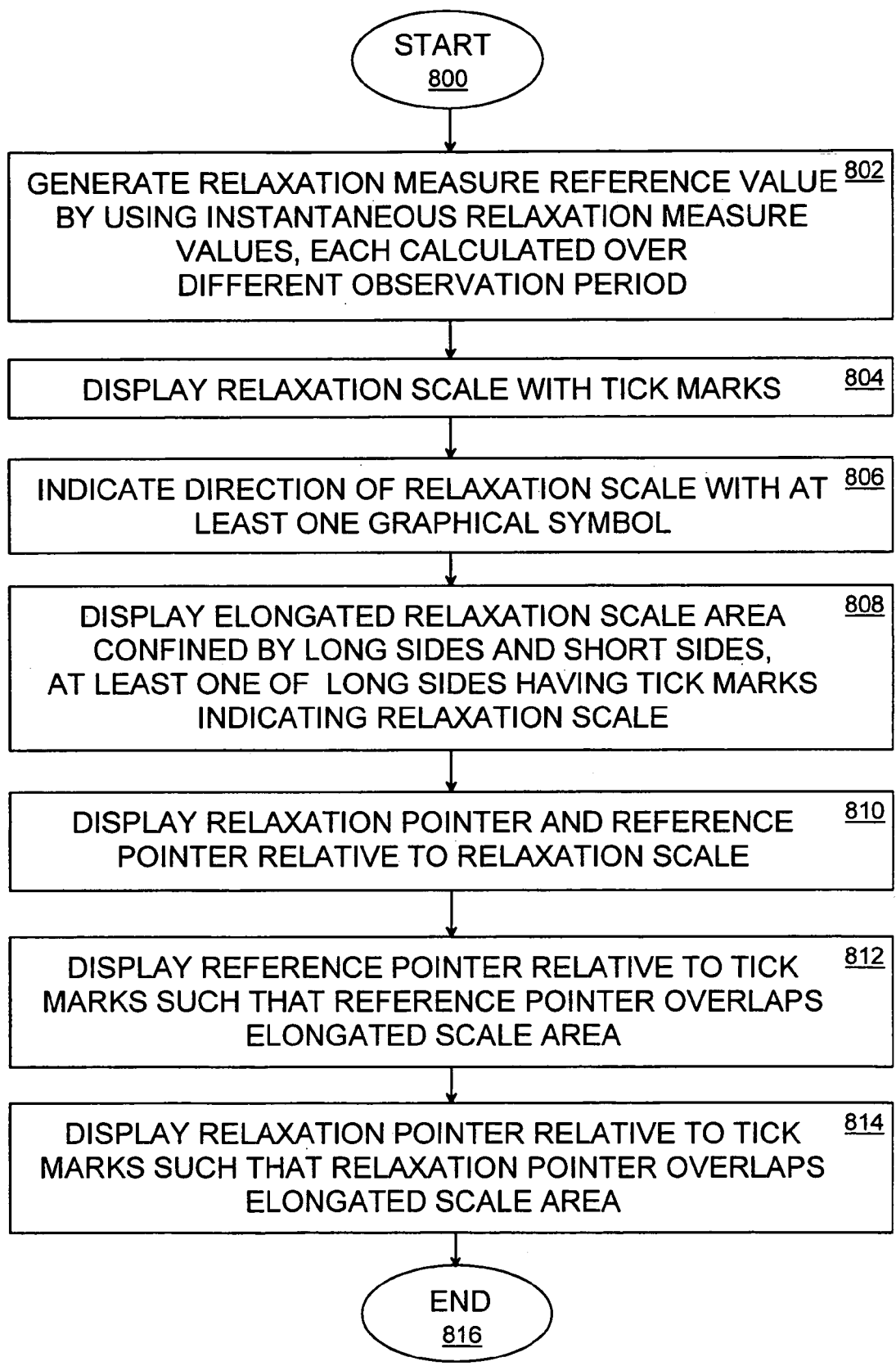
FIG. 8 shows a third example of a methodology according to embodiments of the invention.

In FIG. 8, the method starts in 800.

In 802, a relaxation measure reference value is generated by using a plurality of instantaneous relaxation measure values, each calculated over a different observation period.

In 804, a relaxation scale 506A is displayed with tick marks 502A to 502D.

In 806, the direction of the relaxation scale 506A is indicated with at least one graphical symbol 504A to 504C.

In 808, an elongated scale area 500 defined by long sides 506A, 506A and short sides 508A, 508B is displayed, at least one of the long sides 506A, 506A having tick marks 502A to 502D indicating a relaxation scale.

In 810, the relaxation pointer 422 and the reference pointer 424 are displayed relative to the relaxation scale 506A.

In 812, the reference pointer 424 is displayed relative to the tick marks 502A to 502D such that the reference pointer 424 overlaps the elongated scale area 500.

In 814, the relaxation pointer 424 is displayed relative to the tick marks 502A to 502D such that the relaxation pointer 424 overlaps the elongated scale area 500.

In 816, the method ends.

Figure 9:
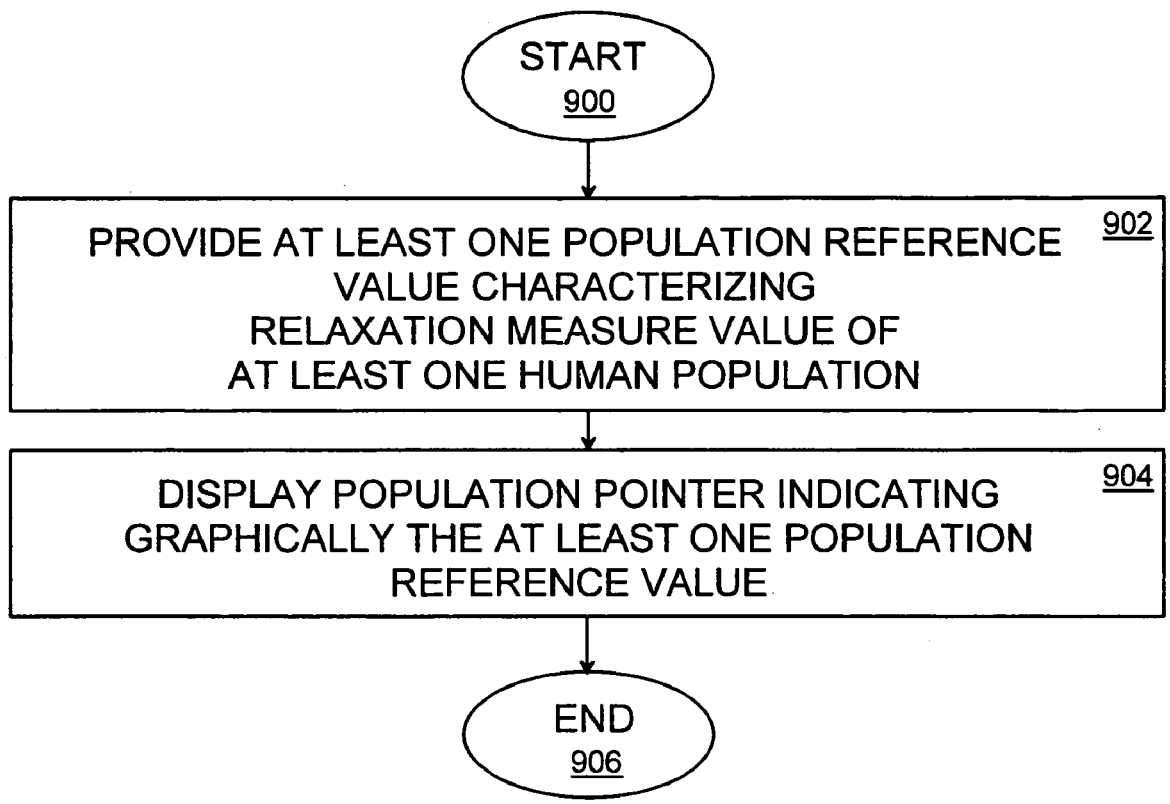
FIG. 9 shows yet another example of a methodology according to embodiments of the invention.

In FIG. 9, the method starts in 900.

In 902, at least one population reference value characterizing a relaxation measure value of at least one human population is provided.

In 904, a population pointer 428 indicating graphically the at least one general relaxation measure value is displayed.

In 906, the method ends.

Even though the invention is described above with reference to an example according to the accompanying drawings, it is clear that the invention is not restricted thereto but it can be modified in several ways within the scope of the appended claims.

The invention claimed is:

1. A user-operated heart rate monitor comprising:
   a timing instant determination unit to determine a plurality of heart beat timing instants from a user's electrocardiogram;
   a relaxation calculator to calculate heart beat rate variation by using heart beat timing instants over an observation period, an instantaneous relaxation measure value being proportional to the heart beat rate variation;
   a relaxation reference generator to calculate a relaxation measure reference value by using a plurality of instantaneous relaxation measure values, each calculated over a different observation period;
   a display configured to display a reference pointer indicating graphically the relaxation measure reference value; and
   wherein the display is further configured to display a relaxation pointer indicating graphically the instantaneous relaxation measure value relative to the reference pointer.

2. The heart rate monitor of claim 1, wherein the display is configured to display a relaxation scale with tick marks; and
   wherein the display is configured to display the relaxation pointer and the reference pointer relative to the relaxation scale.

3. The heart rate monitor of claim 1, wherein the display is configured to display an elongated scale area confined by long sides and short sides, at least one of the long sides having tick marks indicating a relaxation scale,
   wherein the display is configured to display the relaxation pointer relative to the tick marks such that the relaxation pointer overlaps the elongated scale area, and
   wherein the display is configured to display the reference pointer relative to the tick marks such that the reference pointer overlaps the elongated scale area.

4. The heart rate monitor of claim 1, wherein the display is configured to display a relaxation scale, and
   wherein the display is configured to indicate the direction of the relaxation scale with at least one graphical symbol.

5. The heart rate monitor of claim 1, further comprising a population reference unit to provide at least one population reference value characterizing a relaxation measure value of at least one human population, and
   the display is configured to display a population pointer indicating graphically the at least one general relaxation measure value.

6. The heart rate monitor of claim 1, wherein the relaxation reference generator is configured to calculate the relaxation measure reference value as an average of the plurality of instantaneous relaxation measure values.

7. The heart rate monitor of claim 1, wherein the relaxation reference generator is configured to select the relaxation measure reference value from the plurality of instantaneous relaxation measure values on the basis of the magnitudes of the instantaneous relaxation measure values.

8. The heart rate monitor of claim 1, wherein the relaxation reference generator is configured to select a maximum value of the instantaneous relaxation measure values as the relaxation measure reference.

9. A user-operated heart rate monitor comprising:
   a timing instant determining means for determining a plurality of heart beat timing instants from a user's electrocardiogram;
   a relaxation calculating means for calculating heart beat rate variation by using heart beat timing instants over an observation period, an instantaneous relaxation measure value being proportional to the heart beat rate variation; and
   a relaxation reference generating means for calculating a relaxation measure reference value by using a plurality of instantaneous relaxation measure values, each calculated over a different observation period;
   a displaying means configured to display a reference pointer indicating graphically the relaxation measure reference value; and
   wherein the displaying means is further configured to display a relaxation pointer indicating graphically the instantaneous relaxation measure value relative to the reference pointer.

10. The heart rate monitor of claim 9, wherein the displaying means is configured to display a relaxation scale with tick marks, and
    wherein the displaying means is configured to display the relaxation pointer and the reference pointer relative to the relaxation scale.

11. The heart rate monitor of claim 9, wherein the displaying means is configured to display an elongated scale area confined by long sides and short sides, at least one of the long sides having tick marks indicating a relaxation scale,
    wherein the display means is configured to display the relaxation pointer relative to the tick marks such that the relaxation pointer overlaps the elongated scale area, and
    wherein the display means is configured to display the reference pointer relative to the tick marks such that the reference pointer overlaps the elongated scale area.

12. The heart rate monitor of claim 9, wherein the displaying means is configured to display a relaxation scale, and
    wherein the displaying means is configured to indicate the direction of the relaxation scale with at least one graphical symbol.

13. The heart rate monitor of claim 9, further comprising a population reference means for providing at least one population reference value characterizing a relaxation measure value of at least one human population, and the displaying means is configured to display a population pointer indicating graphically the at least one general relaxation measure value.

14. The heart rate monitor of claim 9, wherein the relaxation reference generating means is configured to calculate the relaxation measure reference value as an average of the plurality of instantaneous relaxation measure values.

15. The heart rate monitor of claim 9, wherein the relaxation reference generating means is configured to select the relaxation measure reference value from the plurality of instantaneous relaxation measure values on the basis of the magnitudes of the instantaneous relaxation measure values.

16. The heart rate monitor of claim 9, wherein the relaxation reference generating means is configured to select a maximum value of the instantaneous relaxation measure values as the relaxation measure reference.

17. A method of monitoring a human relaxation level, comprising:
   determining a plurality of heart beat timing instants from a user's electrocardiogram;
   calculating heart beat rate variation by using heart beat timing instants over an observation period, an instantaneous relaxation measure value being proportional to the heart beat rate variation;
   generating a relaxation measure reference value by using a plurality of instantaneous relaxation measure values, each calculated over a different observation period;
   displaying a reference pointer indicating graphically the relaxation measure reference value; and
   displaying a relaxation pointer indicating graphically the instantaneous relaxation measure value relative to the reference pointer.

18. The method of claim 17, further comprising:
   displaying a relaxation scale with tick marks; and
   displaying the relaxation pointer and the reference pointer relative to the relaxation scale.

19. The method of claim 17, further comprising:
   displaying an elongated scale area confined by long sides and short sides, at least one of the long sides having tick marks indicating a relaxation scale;
   displaying the reference pointer relative to the tick marks such that the reference pointer overlaps the elongated scale area; and
   displaying the relaxation pointer relative to the tick marks such that the relaxation pointer overlaps the elongated scale area.

20. The method of claim 17, further comprising:
   displaying a relaxation scale; and
   indicating the direction of the relaxation scale with at least one graphical symbol.

21. The method of claim 17, further comprising:
   providing at least one population reference value characterizing a relaxation measure value of at least one human population; and
   displaying a population pointer indicating graphically the at least one general relaxation measure value.

22. The method of claim 17, further comprising:
   generating the relaxation measure reference value by calculating the relaxation measure reference value as an average of the plurality of instantaneous relaxation measure values.

23. The method of claim 17, further comprising generating the relaxation measure reference value by selecting the relaxation measure reference value from the plurality of instantaneous relaxation measure values on the basis of the magnitudes of the instantaneous relaxation measure values.

24. The method of claim 17, further comprising generating the relaxation measure reference value by selecting a maximum value of the instantaneous relaxation measure values as the relaxation measure reference value.

* * * * *